(12) United States Patent
Chrisikos et al.

(10) Patent No.: US 9,955,325 B2
(45) Date of Patent: Apr. 24, 2018

(54) PERSONAL MEDICAL DEVICE INTERFERENCE MITIGATION

(71) Applicant: QUALCOMM Incorporated, San Diego, CA (US)

(72) Inventors: George Chrisikos, San Diego, CA (US); Richard Wietfeldt, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 15/149,039

(22) Filed: May 6, 2016

(65) Prior Publication Data

US 2017/0325081 A1    Nov. 9, 2017

(51) Int. Cl.
| | | |
|---|---|---|
| *A61N 1/00* | (2006.01) | |
| *H04W 4/18* | (2009.01) | |
| *A61B 5/00* | (2006.01) | |
| *G01S 7/534* | (2006.01) | |
| *G01S 15/32* | (2006.01) | |
| *H04B 5/00* | (2006.01) | |
| *H04W 4/00* | (2018.01) | |
| *H04B 7/00* | (2006.01) | |

(52) U.S. Cl.
CPC ............. *H04W 4/18* (2013.01); *A61B 5/0077* (2013.01); *G01S 7/534* (2013.01); *G01S 15/32* (2013.01); *H04B 5/0031* (2013.01); *H04B 5/0062* (2013.01); *H04B 5/0081* (2013.01); *H04W 4/008* (2013.01); *H04W 4/80* (2018.02)

(58) Field of Classification Search
CPC ...... H04W 4/18; H04W 4/008; A61B 5/0077; G01S 7/534; G01S 15/32; H04B 5/0031; H04B 5/0062; H04B 5/0081; A61N 1/3718

USPC .................... 455/41.2; 607/30, 60
See application file for complete search history.

(56) References Cited

U.S. PATENT DOCUMENTS

| | | | |
|---|---|---|---|
| 5,647,379 A | 7/1997 | Meltzer | |
| 7,196,316 B2 * | 3/2007 | Chan | H04M 1/605 250/221 |
| 7,966,008 B2 | 6/2011 | Graves et al. | |
| 8,406,893 B2 | 3/2013 | Krause et al. | |

(Continued)

FOREIGN PATENT DOCUMENTS

| | | |
|---|---|---|
| JP | 2002141813 A | 5/2002 |
| JP | 2008098869 A | 4/2008 |
| WO | 2017192238 | 11/2017 |

OTHER PUBLICATIONS

International Search Report and Written Opinion—PCT/US2017/026392—ISA/EPO—Jun. 28, 2017.

*Primary Examiner* — Lee Nguyen
(74) *Attorney, Agent, or Firm* — Weaver Austin Villeneuve & Sampson LLP

(57) ABSTRACT

A system may include a sensor system and a control system configured for communication with the sensor system. The sensor system may include an ultrasonic sensor system. The control system may be capable of determining, based at least in part on signals from the ultrasonic sensor system, whether a personal medical device is within a predetermined distance from the mobile device. The control system may be capable of adjusting one or more mobile device settings in response to a determination that the personal medical device is within the predetermined distance of the mobile device.

21 Claims, 8 Drawing Sheets

(56) References Cited

U.S. PATENT DOCUMENTS

| | | | |
|---|---|---|---|
| 8,423,133 | B2 | 4/2013 | Doerr et al. |
| 8,755,902 | B2 | 6/2014 | Lurie et al. |
| 8,913,961 | B2 | 12/2014 | Prather et al. |
| 8,954,030 | B1 * | 2/2015 | Buchheit ............... A61N 1/3925 455/404.1 |
| 9,211,065 | B2 | 12/2015 | Marsh et al. |
| 2005/0146247 | A1 * | 7/2005 | Fisher ................ G01N 29/2406 310/334 |
| 2009/0029793 | A1 * | 1/2009 | Cage ................. A63B 24/0021 473/324 |
| 2013/0165014 | A1 * | 6/2013 | Yang ...................... A63H 33/00 446/175 |
| 2013/0215250 | A1 * | 8/2013 | Pasquero ......... H04N 21/42201 348/78 |
| 2013/0289638 | A1 | 10/2013 | Newman |
| 2014/0005547 | A1 * | 1/2014 | Balasubramanian .. A61B 8/145 600/447 |
| 2014/0057569 | A1 * | 2/2014 | Toivanen ............ H04M 1/7253 455/41.3 |
| 2014/0087633 | A1 * | 3/2014 | Read ...................... B08B 11/02 451/38 |
| 2015/0004996 | A1 * | 1/2015 | Finlow-Bates ......... H04W 4/02 455/456.1 |
| 2016/0117081 | A1 * | 4/2016 | Pujia .................. G06F 3/04842 715/771 |
| 2016/0302692 | A1 * | 10/2016 | Demmer ................ A61B 5/061 |

* cited by examiner

*Figure 3A*
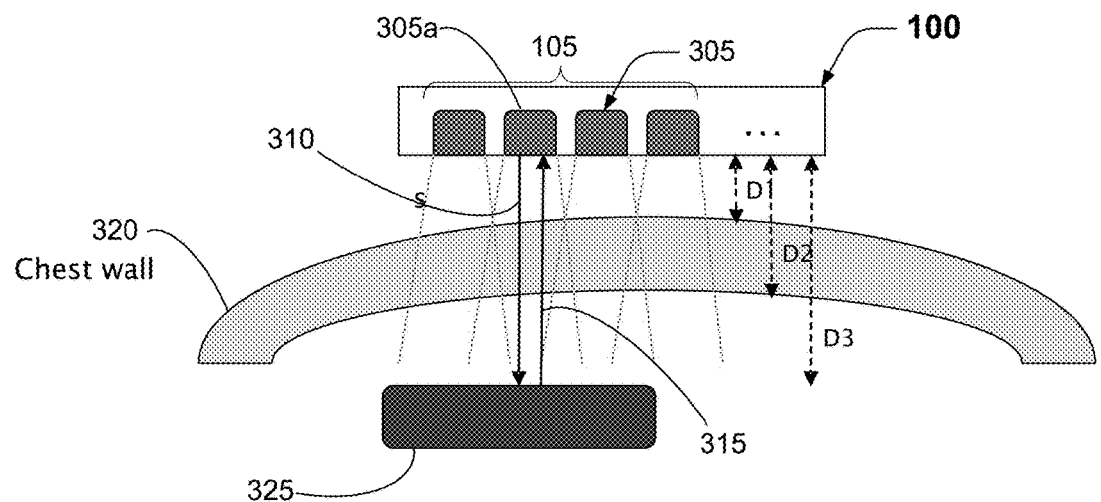
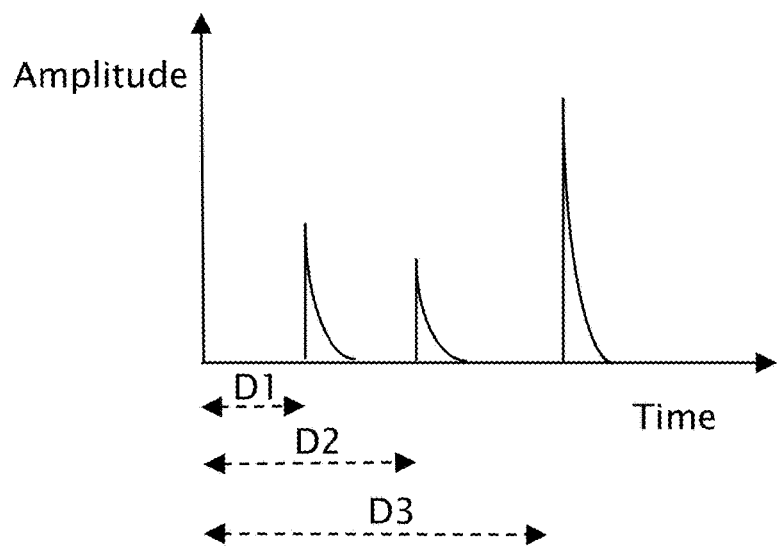
*Figure 3B*

PERSONAL MEDICAL DEVICE INTERFERENCE MITIGATION

TECHNICAL FIELD

This disclosure relates to personal medical devices, including but not limited to implantable medical devices (IMDs) and wearable medical devices. In particular, this disclosure involves mitigating interference that can be caused to personal medical devices by other devices.

DESCRIPTION OF THE RELATED TECHNOLOGY

Interference from mobile phones can cause problems relating to person medical devices, including but not limited to implantable medical devices (IMDs) and wearable medical devices. For example, a pacemaker can mistakenly interpret electromagnetic interference (EMI) from smartphones as being a cardiac signal, causing the pacemaker to briefly stop working. This can lead to a pause in the cardiac rhythm of the patient and may result in syncope. An implantable cardioverter defibrillator (ICD) may interpret a mobile phone's signal as a life-threatening ventricular tachyarrhythmia, leading the ICD to deliver a painful shock. The most problematic phases of a call are ringing and connecting to a network. EMI from mobile phones also can interfere with the operation of blood glucose meters, ear-based implants and retinal implants.

SUMMARY

The systems, methods and devices of the disclosure each have several innovative aspects, no single one of which is solely responsible for the desirable attributes disclosed herein. One innovative aspect of the subject matter described in this disclosure can be implemented in an apparatus that includes a sensor system and a control system. In some examples, a mobile device may be, or may include, the apparatus. In some implementations a mobile device may include a portion of the apparatus. The sensor system may include an ultrasonic sensor system. The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof.

The control system may be capable of determining, based at least in part on signals from the ultrasonic sensor system, whether a personal medical device is within a predetermined distance from the mobile device. The control system may be capable of adjusting one or more mobile device settings in response to a determination that the personal medical device is within the predetermined distance of the mobile device. In some examples, the predetermined distance may correspond with an interference range within which electromagnetic interference from the apparatus (e.g., from a mobile device) can cause interference with operation of the personal medical device.

In some examples, the sensor system may include at least one camera. In some such examples, the control system may be capable of determining that the personal medical device is within the predetermined distance based, at least in part, on data received from the at least one camera. Alternatively, or additionally, the control system may be capable of receiving data from the at least one camera and of determining a position of at least the portion of the person's body based, at least in part, on the data received from the at least one camera.

According to some implementations, the control system may be capable of determining, based on signals received from the sensor system, a position of at least a portion of a person's body. In some such implementations, the control system may be capable of controlling the ultrasonic sensor system to obtain ultrasonic image data of at least the portion of the person's body. Alternatively, or additionally, the control system may be capable of controlling the ultrasonic sensor system to obtain ultrasonic image data from within the portion of the person's body. In some examples, the control system may be capable of determining, based at least in part on the ultrasonic image data, whether the personal medical device is an implantable medical device that may be within, or on, the portion of the person's body.

In some implementations, the control system may be capable of controlling the ultrasonic sensor system to cause transmitted ultrasonic waves to be transmitted in one or more selected directions. According to some such implementations, the ultrasonic sensor system may include an array of individually controllable piezoelectric micromachined ultrasonic transducers (PMUTs) and the control system may be capable of controlling the array of PMUTs to cause constructive interference in the one or more selected directions.

In some examples, the sensor system may include apparatus for receiving radio frequency (RF) signals emitted by the personal medical device. For example, the apparatus may include an RF transmitter capable of transmitting an RF signal for causing a responsive RF signal from a passive radio frequency identification (RFID) tag or a near-field communication tag on the personal medical device.

In some implementations, the ultrasonic sensor system may be capable of receiving ultrasonic signals that are emitted from an active ultrasonic transmitter on the personal medical device. According to some such implementations, the control system may be capable of determining, based at least in part on the ultrasonic signals, whether the personal medical device is within the predetermined distance. In some implementations the control system may be capable of determining the predetermined distance based, at least in part, on one or more contextual indications.

According to some implementations, the apparatus may include at least one induction coil. The control system may be capable of determining the predetermined distance based, at least in part, on input from the at least one induction coil. According to some such implementations, the control system may be capable of controlling the at least one induction coil to provide metal detection functionality. Alternatively, or additionally, the control system may be capable of controlling the at least one induction coil to provide passive or active near-field communications (NFC) functionality.

In some examples, the apparatus may include a user interface. In some such examples, the control system may be capable of varying the predetermined distance according to input received via the user interface. Alternatively, or additionally, the control system may be capable of varying the predetermined distance according to information regarding a device type of the personal medical device. In some implementations, the control system may be capable of varying the predetermined distance according to signals from the ultrasonic sensor system.

In some implementations, the apparatus may include one or more microphones. In some such examples, the control system may be capable of determining whether the personal medical device is within the predetermined distance based, at least in part, on microphone data received from the one or more microphones.

Other innovative aspects of the subject matter described in this disclosure can be implemented in a system that includes a sensor system and a control system configured for communication with the sensor system. In some examples, a mobile device may include the system. In some implementations, a mobile device may be, or may include, only a portion of the system. The sensor system may include an ultrasonic sensor system. The control system may be capable of performing some or all of the methods disclosed herein. In some implementations, the control system may be capable of determining, based at least in part on signals from the ultrasonic sensor system, whether a personal medical device is within a predetermined distance from a mobile device. The control system may be capable of adjusting one or more mobile device settings in response to a determination that the personal medical device is within the predetermined distance of the mobile device.

In some examples, the sensor system may include at least one camera. The control system may be capable of determining that the personal medical device is within the predetermined distance based, at least in part, on data received from the at least one camera.

Other innovative aspects of the subject matter described in this disclosure can be implemented in a method of controlling a mobile device. The method may involve determining, based at least in part on signals from a sensor system that includes an ultrasonic sensor system, whether a personal medical device is within a predetermined distance from the mobile device. The method may involve adjusting one or more mobile device settings in response to a determination that the personal medical device is within the predetermined distance of the mobile device.

In some examples, the sensor system may include at least one camera. The method may involve determining that the personal medical device is within the predetermined distance based, at least in part, on data received from the at least one camera.

In some implementations, the method may involve determining, based on signals received from the sensor system, a position of at least a portion of a person's body. In some such implementations, the method may involve controlling the ultrasonic sensor system to obtain ultrasonic image data of at least the portion of the person's body. Alternatively, or additionally, the method may involve controlling the ultrasonic sensor system to obtain ultrasonic image data from within the portion of the person's body.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in a non-transitory medium having software stored thereon. For example, the software may include instructions for controlling a mobile device to determine, based at least in part on signals from a sensor system that may include an ultrasonic sensor system, whether a personal medical device is within a predetermined distance from the mobile device. The software may include instructions for controlling the mobile device to adjust one or more mobile device settings in response to a determination that the personal medical device is within the predetermined distance of the mobile device.

In some examples, the sensor system may include at least one camera. The software may include instructions for controlling the mobile device to determine that the personal medical device is within the predetermined distance based, at least in part, on data received from the at least one camera.

In some implementations, the software may include instructions for determining, based on signals received from the sensor system, a position of at least a portion of a person's body. According to some such implementations, the software may include instructions for controlling the ultrasonic sensor system to obtain ultrasonic image data of at least the portion of the person's body. In some examples, the software may include instructions for controlling the ultrasonic sensor system to obtain ultrasonic image data from within the portion of the person's body. According to some such examples, the software may include instructions for determining, based at least in part on the ultrasonic image data, whether the personal medical device is an implantable medical device that is within the portion of the person's body.

Other features, aspects, and advantages will become apparent from a review of the disclosure. Note that the relative dimensions of the drawings and other diagrams of this disclosure may not be drawn to scale. The sizes, thicknesses, arrangements, materials, etc., shown and described in this disclosure are made only by way of example and should not be construed as limiting.

BRIEF DESCRIPTION OF THE DRAWINGS

FIG. 3A shows an example of a mobile device obtaining ultrasonic image data from within a person's chest.

FIG. 3B is a graph that shows examples of reflected ultrasonic waves received by the mobile device shown in FIG. 3A.

Like reference numbers and designations in the various drawings indicate like elements.

DETAILED DESCRIPTION

Figure 1:
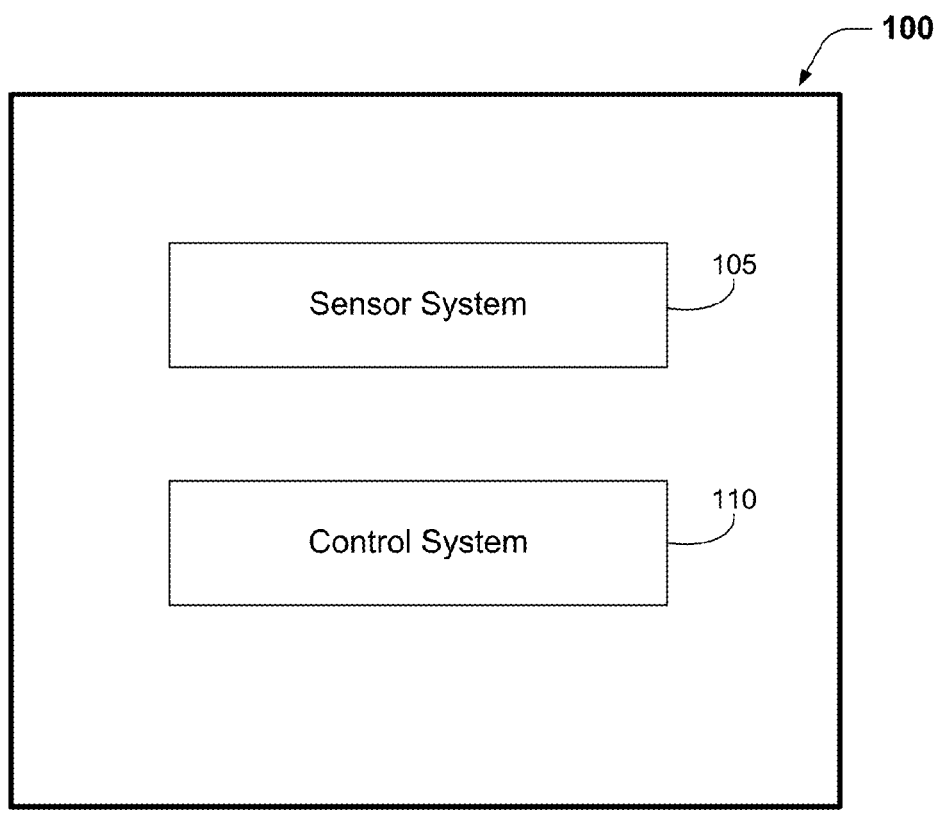
FIG. 1 is a block diagram that shows example components of an apparatus according to some implementations.

The following description is directed to certain implementations for the purposes of describing the innovative aspects of this disclosure. However, a person having ordinary skill in the art will readily recognize that the teachings herein may be applied in a multitude of different ways. The described implementations may be implemented in any device, apparatus, or system that includes a sensor system. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, hand-held or portable computers, netbooks, notebooks, smartbooks, tablets, printers, copiers, scanners, facsimile devices, global positioning system (GPS) receivers/navigators, cameras, digital media players (such as MP3 players), camcorders, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, steering wheels, camera view displays (such as the display of a rear view camera in a vehicle), electronic photographs, electronic billboards or signs, projectors, architectural structures, microwaves, refrigerators, stereo systems, cassette recorders or players, DVD players, CD players, VCRs, radios, portable memory chips, washers, dryers, washer/dryers, parking meters, packaging (such as in electromechanical systems (EMS) applications including microelectromechanical systems (MEMS) applications, as well as non-EMS applications), aesthetic structures (such as display of images on a piece of jewelry or clothing) and a variety of EMS devices. The teachings herein also may be used in applications such as, but not limited to, electronic switching devices, radio frequency filters, sensors, accelerometers, gyroscopes, motion-sensing devices, magnetometers, inertial components for consumer electronics, parts of consumer electronics products, varactors, liquid crystal devices, electrophoretic devices, drive schemes, manufacturing processes and electronic test equipment. Thus, the teachings are not intended to be limited to the implementations depicted solely in the Figures, but instead have wide applicability as will be readily apparent to one having ordinary skill in the art.

In view of the above-described problems that can be caused by EMI from mobile phones, device manufacturers and regulatory institutions, including the US Food and Drug Administration (FDA), recommend a safety distance of 15 to 20 cm between pacemakers or ICDs and mobile phones. However, a person using a mobile phone may not be aware of the potential hazards for his or her personal medical device(s). Even if a person using a mobile phone does not have any personal medical devices, the person may sometimes use a mobile phone close to another person's personal medical device.

Some implementations disclosed herein may include a mobile device that includes a control system and a sensor system. In some implementations, the sensor system may include an ultrasonic sensor system. The control system may be capable of determining the mobile device's proximity to a personal medical device based, at least in part, on sensor data from the sensor system. In some examples, the control system may be capable of determining, based at least in part on signals from the sensor system, whether a personal medical device is within a predetermined distance from the mobile device.

The control system may be capable of adjusting one or more mobile device settings in response to a determination that the personal medical device is within the predetermined distance of the mobile device. In some examples, the personal medical device may be a cardiac device, such as a pacemaker or an ICD. The cardiac device may be an implantable device or a wearable device. In other implementations, the personal medical device may be a blood glucose meter, an ear-based implant or a retinal implant.

Particular implementations of the subject matter described in this disclosure can be implemented to realize one or more of the following potential advantages. By adjusting one or more mobile device settings in response to a determination that the personal medical device is within the predetermined distance of the mobile device, the control system may ameliorate, or even prevent, at least some of the adverse effects of EMI on the personal medical device. For example, by adjusting the mobile device setting(s), the control system may prevent at least some instances of mimicking a life-threatening ventricular tachyarrhythmia and therefore may prevent an ICD from delivering a painful shock. In some examples, by adjusting the mobile device setting(s), the control system may prevent at least some instances of blood glucose meter, ear-based implants or retinal implant malfunction that would otherwise have been caused by EMI from the mobile device.

FIG. 1 is a block diagram that shows example components of a system according to some implementations. In this example, the system 100 includes a sensor system 105 and a control system 110. According to some implementations, the system 100 may be, or may include, a mobile device, such as a smart phone. In some implementations, at least a portion of the sensor system 105 and/or the control system 110 may be included in more than one apparatus. In some examples, a mobile device may include some or all of the control system 110, but may not include all of the sensor system 105. However, the control system 110 may nonetheless be coupled to the entire sensor system 105. As used herein, the term "coupled to" includes being physically coupled for wired communication as well as being configured for wireless communication.

The control system 110 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 110 also may include (and/or be configured for communication with) one or more memory devices, such as one or more random access memory (RAM) devices, read-only memory (ROM) devices and/or other types of non-transitory media. Accordingly, the system 100 may have a memory system that includes one or more memory devices, though the memory system is not shown in FIG. 1. In some examples, the control system 110 may be capable of performing some or all of the methods described herein according to instructions (e.g., software) stored on non-transitory media.

The control system 110 may be capable of performing, at least in part, the methods disclosed herein. For example, the control system 110 may be capable of controlling the sensor system 105 and of receiving and processing data from the sensor system 105, e.g., as described below with reference to FIG. 2 et seq.

In some examples, the sensor system 105 includes an ultrasonic sensor system. Some examples of ultrasonic sensor systems are provided herein. According to some examples, the ultrasonic sensor system may include an ultrasonic transmitter system and an ultrasonic receiver array. In some such examples, the ultrasonic transmitter system may include an ultrasonic plane-wave generator. However, in other implementations the ultrasonic sensor system may include an array of ultrasonic transmitter elements, such as an array of piezoelectric micromachined ultrasonic transducers (PMUTs), an array of capacitive micromachined ultrasonic transducers (CMUTs), etc. Accordingly, in some implementations the ultrasonic receiver array and the ultrasonic transmitter system may be combined in an ultrasonic transceiver system. For example, a piezoelectric receiver layer, PMUT elements in a single-layer array of PMUTs, or CMUT elements in a single-layer array of CMUTs may be used as an ultrasonic transmitter as well as an ultrasonic receiver. Alternatively, or additionally, in some examples the sensor system 105 may include one or more other types of sensors, such as one or more cameras.

Although not shown in FIG. 1, some implementations of the system 100 may include an interface system. In some examples, the interface system may include a wireless interface system. In some implementations, the interface system may include a user interface system, a network interface, an interface between the control system 110 and a memory system and/or an interface between the control system 110 and an external device interface (e.g., a port or an applications processor). In some examples, the interface system may include one or more wired or wireless interfaces between the control system 110 and one or more elements of the sensor system 105. Accordingly, in some such implementations at least a portion of the sensor system 105 and at least a portion of the control system 110 may reside in different devices. For example, at least a portion of the control system 110 may reside in a mobile device and one or more components of the sensor system 105 may reside another device, or in two or more other devices.

Figure 2:
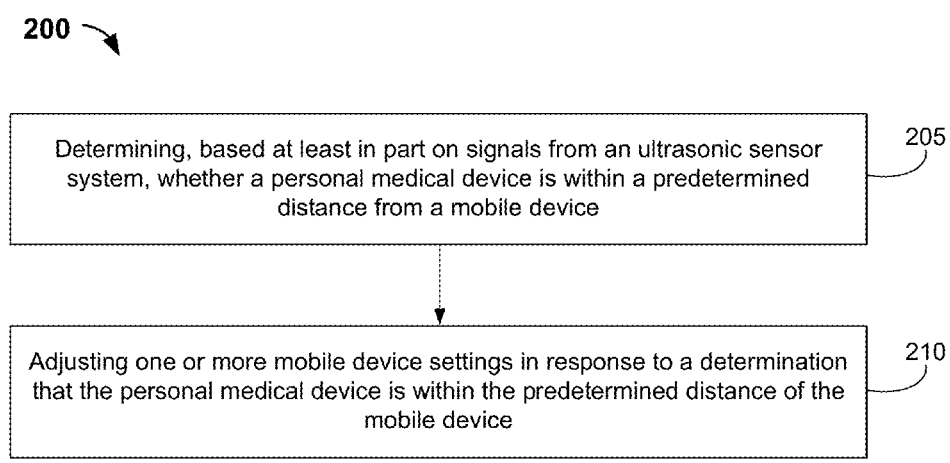
FIG. 2 is a flow diagram that provides example blocks of some methods disclosed herein.

FIG. 2 is a flow diagram that provides example blocks of some methods disclosed herein. The blocks of FIG. 2 (and those of other flow diagrams provided herein) may, for example, be performed by the system 100 of FIG. 1 or by similar apparatus. As with other methods disclosed herein, the method outlined in FIG. 2 may include more or fewer blocks than indicated. Moreover, the operations of methods disclosed herein are not necessarily performed in the order indicated.

Here, block 205 involves determining, based at least in part on signals from a sensor system, whether a personal medical device is within a predetermined distance from a mobile device. In this implementation, the sensor system includes an ultrasonic sensor system. In some examples, the mobile device may be an instance of the system 100 of FIG. 1. The ultrasonic sensor system may, in some instances, be part of the mobile device. Accordingly, in some implementations block 205 may involve determining, based at least in part on signals from an ultrasonic sensor system, whether a personal medical device is within a predetermined distance from a mobile device.

In some examples, the predetermined distance may correspond with an expected or known "interference range" within which the mobile device may potentially interfere with the operation of the personal medical device. As noted above, the FDA recommends maintaining a safety distance of 15 to 20 cm between pacemakers or ICDs and mobile phones.

In some examples, the predetermined distance may correspond with a recommended safety distance. For instance, if a recommended safety distance is in the range of 15 to 20 cm, in some examples the predetermined distance may be in the range of 15 to 20 cm, e.g., 20 cm.

The distance between a mobile device and a personal medical device may change over time, due to the relative motion of the mobile device and a personal medical device. For example, a person using a personal medical device and/or a person in possession of a mobile device may be moving. Therefore, according to some implementations, the predetermined distance may be greater than an outer limit of a recommended safety distance. For example, if a recommended safety distance is in the range of 15 to 20 cm, in some examples the predetermined distance may be more than 20 cm, e.g., 30 cm, 40 cm, 50 cm, 1 meter, 2 meters, etc. Such implementations have the potential advantage of allowing additional time for determining whether a personal medical device is within a predetermined distance from a mobile device and, if so, for taking action before the mobile device could cause interference with the personal medical device.

The predetermined distance may vary, depending on the particular implementation, the specifications of particular personal medical devices and/or the specifications of particular mobile devices. In some implementations, the predetermined distance may be changeable, according to user input, according to information regarding particular personal medical devices and/or according to information regarding particular mobile device specifications, etc. For example, the predetermined distance may be changeable according to stored information, accessible by a control system, regarding the transmission power of a mobile device.

In this example, block 210 involves adjusting one or more mobile device settings in response to a determination that the personal medical device is within the predetermined distance of the mobile device. As noted above, the most likely times during which EMI from a mobile phone may interfere with the operation of a personal medical device are during a call ringing process and during a process of connecting to a telephone network. Therefore, in some examples block 210 may involve adjusting the transmission power of a mobile device. Alternatively, or additionally, block 210 may involve disabling a ring function of a mobile device and/or disabling a network connection for placing or receiving a call. According to some examples, block 210 may involve controlling a mobile device to enter a sleep mode or an airplane mode. In some implementations, block 210 may involve turning off one or more processors. In some instances, block 210 may involve alerting a user (e.g., by controlling a speaker of the mobile device to provide audio prompts) to move the mobile device away from an area in which the personal medical device is located.

As noted above, in some instances the sensor system may include one or more cameras. According to some such implementations block 205 may involve determining, based at least in part on camera data received from a camera, whether a personal medical device is within a predetermined distance from a mobile device. As used herein, the term "camera data" is not limited to image data, but instead may encompass one or more other types of data that may be received from a camera (or from a camera system that includes one or more cameras), such as location data, inertial sensor data, etc. In some examples, the camera data may be processed, at least to some degree, before it is provided to a control system. According to some such examples, a camera or a camera system may be capable of implementing one or more computer vision algorithms. In some implementations the camera data may include the output of one or more computer vision algorithm that can automatically detect and classify raw image data. In some such implementations, a camera or a camera system may be capable of providing simultaneous localization and mapping (SLAM) functionality. According to some implementations, block 205 may involve determining whether a personal medical device is within a predetermined distance from a mobile device based, at least in part, on signals from an ultrasonic sensor system and also on camera data received from the camera. Various examples are disclosed herein.

In some examples, the control system may be capable of determining whether the personal medical device is within the predetermined distance based, at least in part, on contextual indications. For example, a user may be able to input preferences, via a user interface of the mobile device, to indicate that he or she has a personal medical device, that a family member has a personal medical device, etc. This information may be used in conjunction with one or more sensors of the mobile device (such as proximity sensors, a camera, one or more microphones, etc.) to determine proximity to a person's chest, belly or other area in which an IMD is implanted or where another type of personal medical device may be located.

In some implementations, the control system may be capable of controlling the sensor system to determine the position of at least a portion of a user's body and/or at least a portion of a nearby person's body. In some such examples, a control system of the mobile device may be capable of determining, based on signals received from the sensor system, the positions of more than one person's body. Accordingly, the body may or may not correspond with a person who is in possession of a mobile device. In some examples, the control system of the mobile device may be capable of determining, based on signals received from the sensor system, a position of at least a portion of the body of another person having a personal medical device. In some such examples, the owner or user of a mobile device may not have any personal medical devices, but yet in some implementations the mobile device may be capable of determining the proximity of another person's personal medical device and/or of adjusting one or more mobile device settings in response to such proximity detection.

According to some such examples, a position of at least a portion of a person's body may be determined according to camera data. In some such implementations, the control system may be capable of applying one or more computer vision algorithms to determine the mobile device's orientation and proximity to a person's chest, head, arms, belly, etc., according to image data from the camera(s). According to some such examples, the control system may be capable of object recognition functionality. For example, the control system may be capable of finding and identifying certain types of objects in an image or video sequence. The object types may, for example, include human faces, heads, hands, arms, legs, torsos, etc.

Alternatively, or additionally, the position of at least the portion of the person's body may be determined according to signals received from an ultrasonic sensor system. For example, in some implementations the control system may be capable of controlling the ultrasonic sensor system for ultrasonic ranging functionality. In some such examples, the control system may be capable of controlling the ultrasonic sensor system to transmit ultrasonic waves in a plurality of directions and of determining the locations of nearby objects according to reflected ultrasonic waves that are subsequently received by the ultrasonic sensor system.

The air/body interface provides a significant acoustic impedance contrast. Accordingly, by controlling an ultrasonic transmitter to emit ultrasonic waves and measuring the time at which reflected ultrasonic waves are received by an ultrasonic receiver array, the control system may determine the travel time to a surface of the user's chest, head, arms, belly, etc., as well as determining the travel times to surfaces of one or more other nearby people's bodies.

In some implementations, the control system may be capable of converting such travel times to distances. According to some such implementations, the control system may be capable of determining the position of one or more surfaces human bodies, walls and/or other objects in three-dimensional space, relative to the position of the mobile device. Some such implementations may simply convert travel times to distances by using a constant speed of sound in air, such as an average speed under typical conditions. However, the speed of sound in air varies significantly according to temperature, from about 330 m/sec at −1 degree Centigrade to about 358 m/sec at 45 degrees Centigrade. The speed of sound in air also varies somewhat according to changes in atmospheric pressure and humidity. However, the speed of sound in air generally varies according to the formula $v=331$ m/s+0.6 m/s/C*T, for a given pressure and level of humidity. Accordingly, some mobile device implementations may be capable of determining an ambient temperature and of converting travel times to distances by using a variable speed of sound in air, estimated according to the ambient temperature.

Whether the position of the portion of the person's body is determined according to signals received from an ultrasonic sensor system, according to camera data, or both, in some implementations the control system may be capable of controlling the ultrasonic sensor system to obtain ultrasonic sensor data from within the portion of the person's body. As used herein, such ultrasonic sensor data may be referred to as "ultrasonic image data," although the ultrasonic sensor data provided to the control system may include various types of data, depending on the particular implementation. For example, in some implementations the ultrasonic sensor data provided to the control system may include raw ultrasonic sensor data, whereas in some examples the ultrasonic sensor data may be processed before being provided to the control system. For example, in some implementations the ultrasonic sensor system may be capable of filtering, gain control, noise cancellation and/or other types of processing. According to some such implementations, the control system may be capable of determining, based at least in part on the ultrasonic image data, whether the personal medical device is an implantable medical device that is within the portion of the person's body.

FIG. 3A shows an example of a mobile device obtaining ultrasonic image data from within a person's chest. The sensor system 105 shown in FIG. 3A includes an ultrasonic sensor system. In this implementation, the ultrasonic sensor system includes an array of ultrasonic transceivers. In alternative implementations, the mobile device may include an ultrasonic transmitter system and an array of ultrasonic receivers. However, in this example the ultrasonic sensor system includes an array of individually controllable piezoelectric micromachined ultrasonic transducers (PMUTs).

Here, the PMUT element 305a has generated the transmitted ultrasonic waves 310 and is shown receiving the reflected ultrasonic waves 315. In this example, the transmitted ultrasonic waves 310 are capable of penetrating the chest wall 320. FIG. 3A indicates the distance D1 to the outer portion of the chest wall 320, the distance D2 to the inner portion of the chest wall 320 and the distance D3 to a surface of an implantable medical device (IMD) 325.

FIG. 3B is a graph that shows examples of reflected ultrasonic waves received by the mobile device shown in FIG. 3A. In this example, the reflected ultrasonic waves 315 have been received by the PMUT element 305a shown in FIG. 3A. Accordingly, the graph shown in FIG. 3B indicates examples of the amplitudes of the reflected ultrasonic waves 315 received by the PMUT element 305a. The times corresponding with depths D1, D2 and D3 are indicated near the horizontal axis. In this example, the IMD 325 includes metal. Because of the large impedance contrast between the IMD 325 and the surrounding tissue, the IMD causes a high-amplitude reflection at a time corresponding with the depth D3. The smaller impedance contrasts at the outer portion of the chest wall 320 and at the inner portion of the chest wall 320 cause lower-amplitude reflection at times corresponding with the depths D1 and D2. Accordingly, the reflection corresponding with the IMD 325 can readily be identified in this example.

Although FIG. 3A shows the mobile device being positioned close to a user's chest and in a particular orientation relative to the user's chest, this is merely an example. Some implementations may be capable of determining a location of a personal medical device, such as the IMD 325, with requiring the mobile device to be positioned in such a manner. Some such implementations may be capable of determining a location of a personal medical device without any conscious effort being made by a user. In some such implementations, the user may not need to be aware that the mobile device is attempting to detect a personal medical device or determining a location of a personal medical device.

As noted above, in some implementations the control system may be capable of controlling the sensor system to determine the position of at least a portion of a user's body and/or the bodies of nearby people. According to some such implementations, the control system may direct transmitted ultrasonic waves to a selected area of a person's body, such as the person's chest, in order to evaluate whether the person has an IMD in the selected area. In some such implementations, the direction of transmission may be selected according to the output of a computer vision algorithm, based on camera data, indicating the current location of the selected area of a user's body. Alternatively, or additionally, the direction of transmission may be selected according to ultrasonic image data received by an ultrasonic sensor system.

In some implementations, the control system may be capable of controlling the ultrasonic sensor system to cause ultrasonic waves to be transmitted in one or more selected directions. For example, the ultrasonic sensor system may be capable of beam steering via constructive interference of the transmitted ultrasonic waves. In some examples, the ultrasonic transmitter system may include an array of piezoelectric micromachined ultrasonic transducer (PMUT) elements and/or capacitive micromechanical ultrasonic transducer (CMUT) elements, which may be individually controllable via the control system in order to cause constructive and destructive interference in selected directions.

Figure 4A:
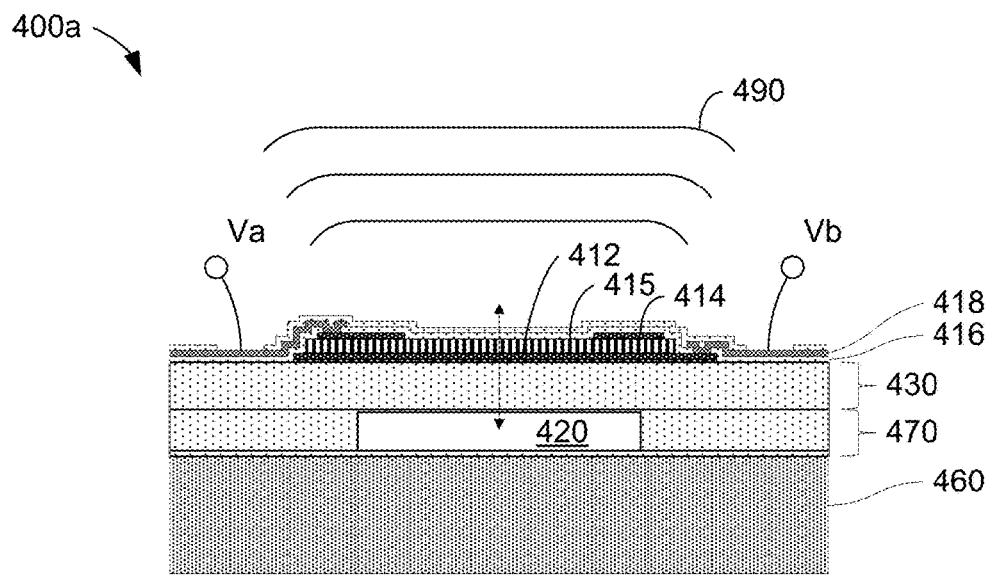
FIG. 4A shows an example of a PMUT element.

FIG. 4A shows an example of a PMUT element. The PMUT element 400a may have one or more layers of piezoelectric material such as aluminum nitride (AlN) or lead zirconium titanate (PZT) in a piezoelectric layer that may be used to actuate the PMUT element to generate ultrasonic waves or to detect received ultrasonic waves. The piezoelectric layer stack may include a lower electrode layer 112, a piezoelectric layer 415, and an upper electrode layer 414, with the piezoelectric layer 415 sandwiched between at least a portion of the lower and upper electrodes 112 and 414. One or more dielectric layers 416 may provide electrical isolation for a metal interconnect layer 418, while allowing connections to lower and upper electrodes 112 and 414, respectively. The piezoelectric layer stack may be disposed on, below or above a mechanical layer 430. An anchor structure 470 may support the PMUT membrane or diaphragm that is suspended over a cavity 420 and a substrate 460. The substrate 460 may have TFT circuitry for driving and sensing the PMUT 400a and for generating a visual display. The piezoelectric layer stack and mechanical layer 430 may flex, bend or vibrate in response to drive voltages Va and Vb applied across the electrode layers 414 and 112, respectively. Vibrations of the PMUT element 400a may generate ultrasonic waves 490 at a frequency determined by the excitation frequency of the drive voltages. Ultrasonic waves striking the PMUT diaphragm may result in generation of sense voltages Va and Vb with flexing of the diaphragm. An underlying cavity 420 allows for deflections of the PMUT element 400a without contacting the underlying substrate 460. According to some examples, the operating frequencies of the PMUT elements 400a may be tailored for high-frequency operation, low-frequency operation, medium-frequency operation, or a combination of frequencies.

Figure 4B:
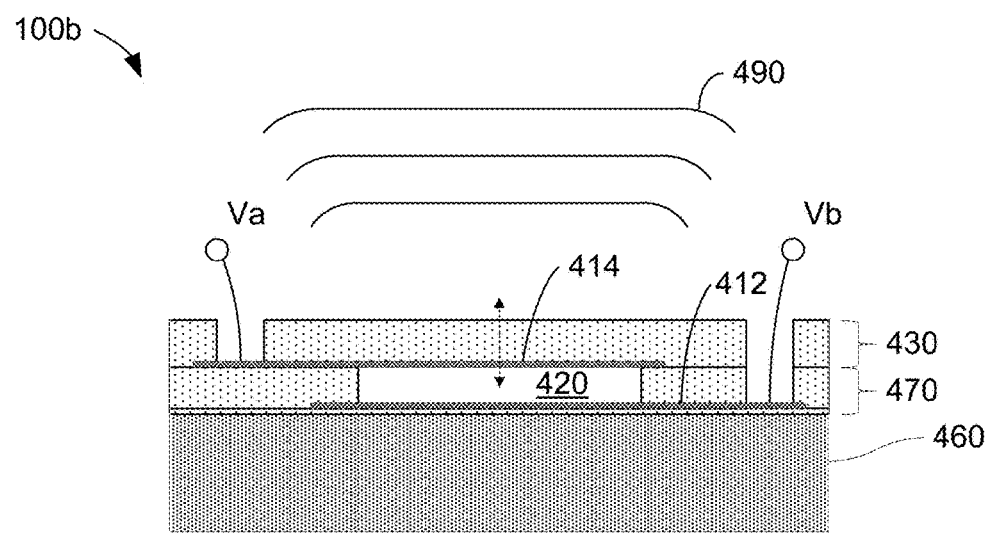
FIG. 4B shows an example of a CMUT element.

FIG. 4B shows an example of a CMUT element. The CMUT element 400b may have a mechanical layer 430 supported above a cavity 420 and a substrate 460 by an anchor structure 470. Lower electrode 112 on the substrate below the cavity and upper electrode 414 above the cavity 420 may be driven with an excitation voltage applied to terminals Va and Vb to generate ultrasonic waves 490. A potential difference between electrodes 112 and 414 causes an electrostatic force to be generated that attracts the flexible diaphragm of CMUT element 400b downwards towards the substrate. As electrostatic forces are attractive in this configuration whether Va is larger than Vb or Vb is larger than Va, one of the electrodes may need to be biased at a relatively high DC voltage to allow small applied AC voltages to drive the diaphragm up and down. Biasing is also required for sensing deflections of the CMUT diaphragm above the cavity 420.

PMUT element 400a, while somewhat more complex to fabricate than CMUT element 400b, generally requires smaller operating voltages than the CMUT element 400b to generate similar acoustic power. The PMUT element 400a does not suffer from consequential pull-in voltages for electrostatic devices such as CMUT element 400b, allowing a fuller range of travel. Furthermore, CMUT elements 400b may require significantly higher bias voltages to allow detection of incoming ultrasonic waves.

Although there are some differences between PMUT and CMUT elements, the phrase "PMUT array" may be used herein to refer to an array that includes PMUT elements, CMUT elements, or both PMUT and CMUT elements. In some implementations, the sensor system 105 shown in FIG. 1 may include such a PMUT array. In some implementations, the control system 110 may be capable of addressing at least a portion of the PMUT array for wavefront beam forming, beam steering, receive-side beam forming, and/or selective readout of returned signals. In some implementations, the control system 110 may control at least a portion of the PMUT array to produce wavefronts of a particular shape, such as planar, circular (spherical) or cylindrical wave fronts.

According to some implementations, the control system 110 may be capable of controlling the magnitude and/or phase of at least a portion of the PMUT array to produce constructive or destructive interference in desired locations. For example, the control system 110 may control the magnitude and/or phase of at least a portion of the PMUT array to produce constructive interference towards a location in which at least a portion of a person's body has been detected.

The generation and emission of planar ultrasonic waves (e.g., plane waves) may be achieved by exciting and actuating a large number of PMUT elements in the PMUT array in a simultaneous manner, which may generate an ultrasonic wave with a substantially planar wavefront. Actuation of single PMUT elements in the PMUT array may generate substantially spherical waves in a forward direction, with the PMUT element serving as the source of the spherical waves. Alternatively, the spherical waves may be generated by selecting and exciting an individual PMUT element (the center element), determining a first ring of PMUT elements around the center PMUT element and actuating the first ring in a delayed manner, determining a second ring of PMUT elements around the first ring and actuating the second ring in a further delayed manner, and so forth as needed. The timing of the excitations may be selected to form a substantially spherical wavefront. Similarly, a cylindrical wave may be generated by selecting and exciting a group of PMUT elements in a row, with the row of PMUT elements serving as the source of the cylindrical waves. Alternatively, the cylindrical waves may be generated by selecting and exciting a row of PMUT elements (the center row), determining and exciting adjacent rows of PMUT elements equidistant from the center row with a controlled time delay, and so forth. The timing of the excitations may be selected to form a substantially cylindrical wavefront.

While exciting an array of PMUT elements simultaneously may produce an ultrasonic plane wave traveling perpendicular to the PMUT array, phase control of PMUT excitation may allow redirection of the plane wave in various directions, depending on the amount of phase delay. For example, if a phase delay of 10 degrees is applied to adjacent rows of PMUT elements that are positioned a distance of one-tenth of a wavelength apart, then the wavefront will transmit a plane wave at an angle of about 15.5 degrees from the normal. Scanning a plane wave at different angles while detecting echoes (reflected portions) from an object positioned in front of the PMUT array may allow detection of the approximate shape, distance and position of the object. Consecutive determinations of object distance and position may allow determination of air gestures.

Other forms of transmit-side beam forming may be utilized. For example, a set of PMUT elements in the PMUT array may be fired in a manner to focus the wavefront of an ultrasonic wave at a particular location in front of the array. For example, the focused wavefront may be cylindrical or spherical by adjusting the timing (e.g., phase) of selected PMUT elements so that the generated wave from each selected PMUT element arrives at a predetermined location in the region in front of the PMUT array at a predetermined time. Focused wavefronts may generate appreciably higher acoustic pressure at a point of interest, and the reflected signal from an object at the point of interest may be detected by operating the PMUT array in a receive mode. The wavefronts emitted from various PMUT elements may interfere constructively in the focal region. The wavefronts from various PMUT elements may interfere destructively in regions near the focal region, providing further isolation of the focused beam energy (amplitude) and increasing the signal-to-noise ratio of the return signal. Similarly, control of the phase at which detection occurs for various PMUT elements in the PMUT array allows receive-side beam forming, in which the return signals may be correlated with distance from a region in space and combined accordingly to generate an image of an object in the detection region. Controlling the frequency, amplitude and phase of the transmitted waves from PMUT elements in the PMUT array may also allow beam shaping and beam forming. In some implementations, not all of the PMUT elements in the PMUT array need be read out for each mode of operation or for each frame. To save processing time and reduce drain on battery life, return signals detected by a select group of PMUT elements may be read out during acquisition. The control system 110 may be configured to address a portion of the PMUT array for wavefront beam forming, beam steering, receive-side beam forming, or selective readout of returned signals.

Figure 5:
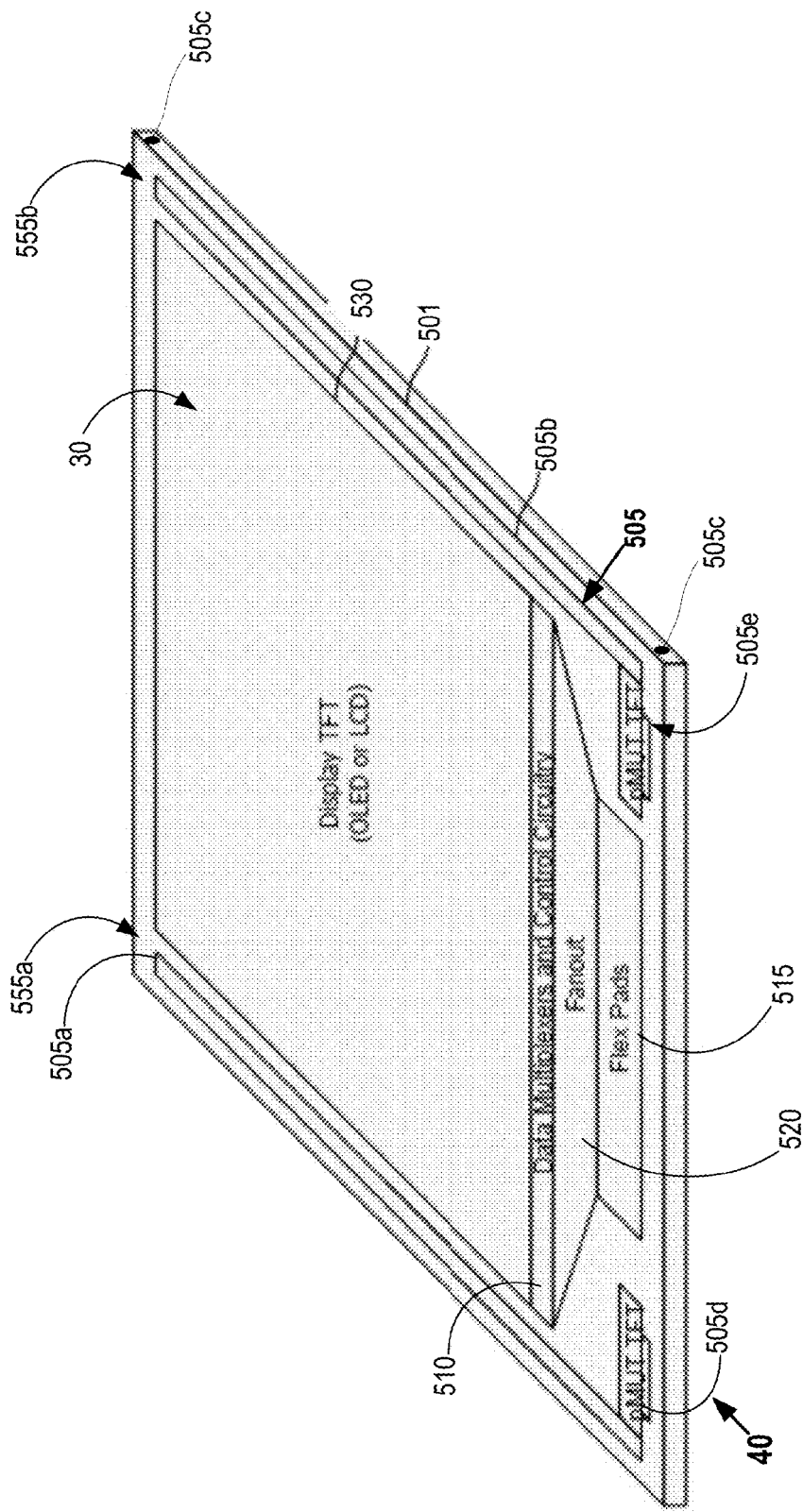
FIG. 5 shows examples of PMUT arrays disposed in peripheral areas of a display.

FIG. 5 shows examples of PMUT arrays disposed in peripheral areas of a display. As with other implementations disclosed herein, the numbers, types, sizes and arrangements of elements are made by way of example. Other implementations may include other numbers, types, sizes and/or arrangements of elements. In the example shown in FIG. 5, thin-film transistor (TFT) circuitry 500 for the PMUT array 505 is disposed on the same substrate (the substrate 501) as TFT circuitry 530 for a display 30. The display 30 may, in some examples, be a liquid crystal display (LCD) or an organic light-emitting diode (OLED) display. Here, the data multiplexer and control circuitry 510 are connected to the flex pads 515 via the fanout region 520. In this example, the area of the display 30 is approximately coextensive with the area of the TFT circuitry 530. In some implementations, one or more flex cables may be attached and electrically connected to at least a portion of the flex pads 515. For example, a flex cable may be shared between circuitry for controlling at least a portion of the PMUT array 505 and TFT circuitry 530 for controlling the display.

In this example, the PMUT array 505 includes PMUT sub-arrays 505a-505e. In this implementation, the PMUT sub-arrays 505a-e are disposed outside of the active display area. In alternative implementations, one or more PMUT arrays 505 may be disposed inside of the active display area. According to this example, the PMUT sub-arrays 505a and 505b extend along at least a portion of the sides 555a and 555b, respectively, of the display device 40. Here, a PMUT element 505d is positioned along the side 555a near one corner of the display device 40, and PMUT element 505e is positioned along the side 555b near a second corner of the display device 40. In some examples, third and fourth PMUT elements may be positioned near a third and fourth corner of the display device 40. Having PMUT elements configured near each of the four corners of the display device 40 may allow for gesture detection via triangulation of a finger, hand or other object positioned above the display device 40. More than one PMUT element in a sub-array may be configured in each corner or along one or more sides of the display device 40. In some examples, the PMUT sub-arrays 505a and 505b also may be configurable for gesture detection. In this implementation, the PMUT sub-arrays 505a and 505b may be driven by TFT circuitry 500, which may be disposed in at least two corners of the display device 40. In some implementations, the TFT circuitry 500 and one or more of the PMUT arrays 505 may be configurable for other functionality, such as fingerprint sensor functionality or button functionality.

According to this implementation, the PMUT array 505 includes PMUT sub-arrays 505c on one or more sides of the display device 40. In some examples, the PMUT array 505 includes PMUT sub-arrays 505c on all sides of the display device 40. In this implementation at least the PMUT sub-arrays 505c are capable of providing ultrasonic ranging functionality. According to some implementations, one or more of the PMUT sub-arrays 505a, 505b, 505d and 505e also may be capable of providing ultrasonic ranging functionality. According to some implementations, one or more of the PMUT sub-arrays 505*a*-505*e* also may be capable of providing beam steering functionality, e.g., as described above. Although not shown in FIG. 5, in some implementations the display device 40 may include one or more cameras.

According to some examples, the operating frequencies of some PMUT elements may be tailored for high-frequency operation, low-frequency operation, medium-frequency operation, or operation at a combination of frequencies. Such implementations are potentially advantageous in view of the fact that relatively higher-frequency ultrasonic waves are capable of providing relatively higher resolution, but are attenuated more rapidly than relatively lower-frequency ultrasonic waves. Accordingly, a low-frequency mode may be more suitable for ultrasonic ranging or for gesture detection, whereas a high-frequency mode may be more suitable for fingerprint imaging.

In some implementations, a control system may be capable of making a determination whether to operate at least a portion of the PMUT array 505 in a low-frequency mode, a medium-frequency mode and/or a high-frequency mode. The control system may be capable of controlling at least a portion of the PMUT array 505 to operate in the low-frequency mode and/or the high-frequency mode, according to the determination. The display device may include an interface system. In some examples, the determination may be made, at least in part, according to input received from the interface system.

In some examples, the low-frequency mode may correspond to a gesture detection mode, wherein free-space gestures near the display may be detected. In some examples, the low-frequency mode may correspond to an ultrasonic ranging mode. According to some implementations, the low-frequency mode may correspond to a frequency range of approximately 50 kHz to 200 kHz. However, in some implementations the low-frequency mode may correspond to a frequency range of less than 50 kHz, e.g., of approximately 30 kHz, approximately 35 kHz, approximately 40 kHz, approximately 45 kHz, etc.

According to some implementations, the high-frequency mode may correspond to a frequency range of approximately 1 MHz to 25 MHz. In some examples, the high-frequency mode may correspond to a fingerprint sensor mode or a stylus detection mode.

In some implementations, a mobile device may be capable of receiving signals that are emitted from a personal medical device. For example, a sensor system of the mobile device may include an ultrasonic sensor system that is capable of receiving ultrasonic signals that are emitted from an active ultrasonic transmitter on the personal medical device. A control system of the mobile device may be capable of determining, based at least in part on the ultrasonic signals, whether the personal medical device is within the predetermined distance.

Alternatively, or additionally, the mobile device may include one or more microphones. The control system may be capable of determining whether the personal medical device is within the predetermined distance based, at least in part, on microphone data received from the one or more microphones. In some examples, control system may be capable of determining that a sound detected by the one or more microphones is a sound that is characteristic of a particular type of personal medical device, such as the sound of a particular type of pacemaker.

According to some implementations, a mobile device may be capable of receiving radio frequency (RF) signals emitted by a personal medical device. According to some such implementations, the personal medical device may have an active or passive radio frequency identification (RFID) tag or a near-field communication tag that is capable of emitting RF signals. The RF signals may, in some examples, include information that identifies the type of personal medical device. A control system of the mobile device may be capable of determining the type of personal medical device according to the received RF signals.

Figure 6:
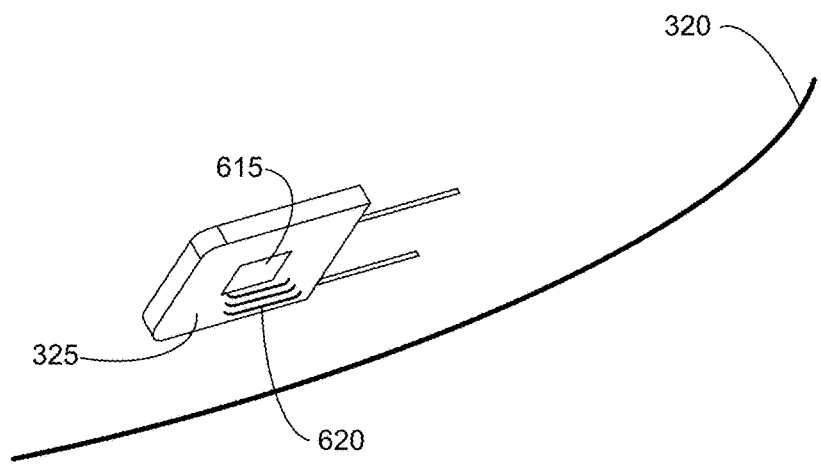
FIG. 6 shows an example of a mobile device that is capable of receiving RF signals emitted by a personal medical device.
Figure 6:
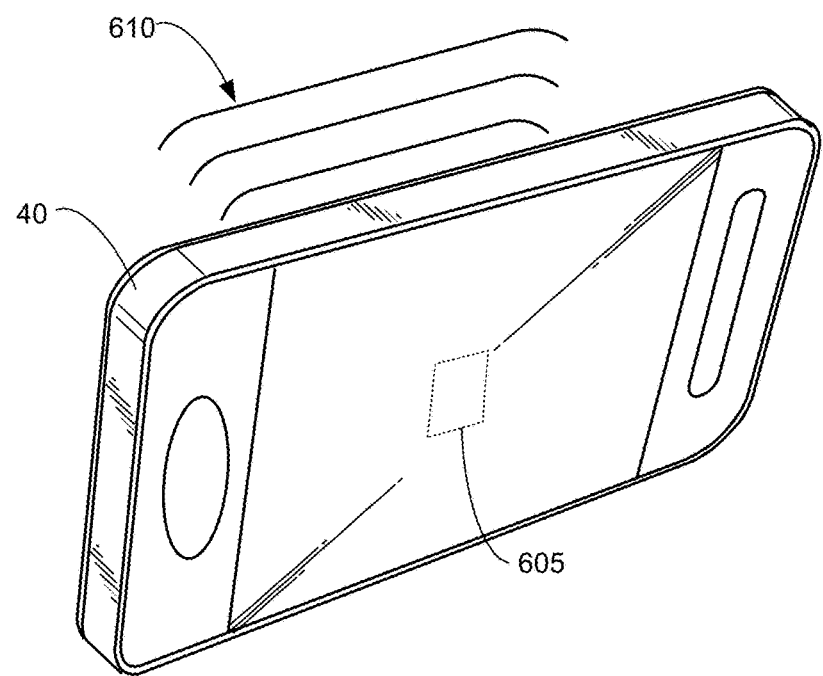

FIG. 6 shows an example of a mobile device that is capable of receiving RF signals emitted by a personal medical device. In this example, the mobile device is a display device 40 that includes an RF transceiver module 605. At the time depicted in FIG. 6, the RF transceiver module 605 is emitting RF waves 610. An IMD 325, which is an implantable cardioverter defibrillator (ICD) within a chest wall 320 in this example, is equipped with a passive RFID tag 615. The passive RFID tag 615 is shown transmitting RF waves 620 in response to the RF waves 610. In this implementation, a control system of the display device 40 is capable of detecting the IMD 325 according to the RF waves 620 received by the RF transceiver module 605.

In some such examples, the detection range of the RF waves 620 (in other words, the distance within which the RF transceiver module 605 is capable of detecting the RF waves 620) may correspond with a predetermined distance between the display device 40 and the IMD 325 that will trigger a control system of the display device 40 to adjust one or more settings of the display device 40 in order to prevent, or at least to ameliorate, the effects of EMI from the display device 40. According to some such examples, the detection range of the RF waves 620 may be approximately 20 cm, or slightly more than 20 cm (e.g., 25 cm, 30 cm, 35 cm, 40 cm, etc.).

Figure 7:
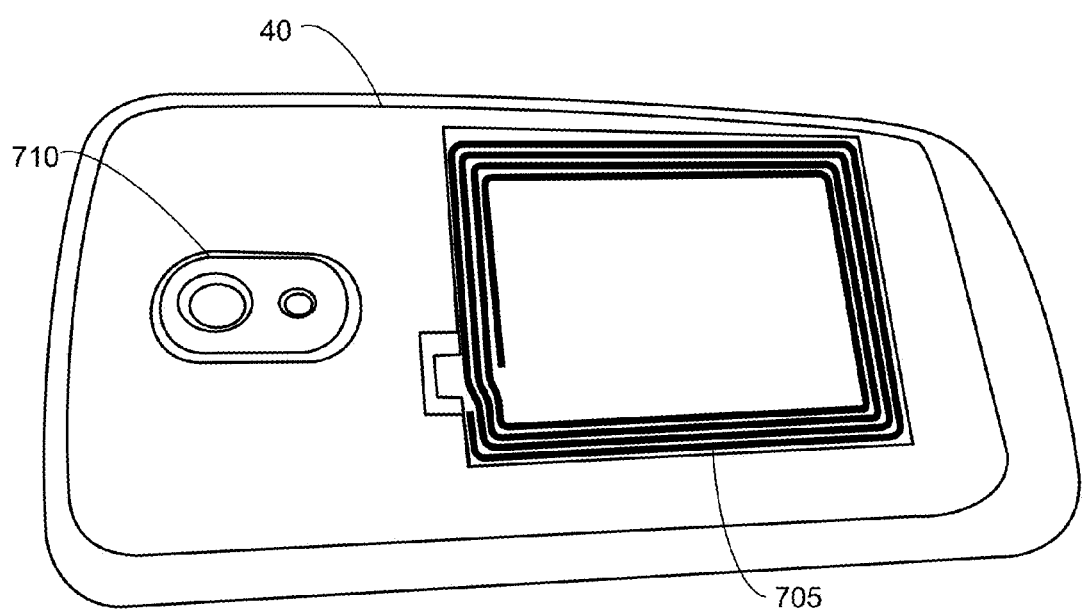
FIG. 7 shows an example of a mobile device that includes an induction coil.

FIG. 7 shows an example of a mobile device that includes an induction coil. Here, the display device 40 includes an induction coil 705 and a camera system 710, which includes two cameras. A control system of the display device 40 may operate the induction coil 705 in a variety of ways, depending on the particular implementation. For example, the induction coil 705 may be used to sense the material and/or size of a personal medical device, to read RF signals from an RFID tag on the personal medical device, etc.

In some examples, the control system may be capable of identifying a personal medical device and/or of determining the proximity of the personal medical device according to an electromagnetic interference signature of the medical device. Electromagnetic waves from the personal medical device may, for example, be detected by the induction coil 705. The electromagnetic interference signature of the personal medical device may be determined by a control system of the display device 40, e.g., according to temporal and/or frequency characteristics of the received electromagnetic waves.

In some implementations, the display device 40 may be capable of passive or active near-field communication (NFC) functionality. According to some such implementations, the personal medical device also may be equipped with an induction coil, which may be a passive or an active induction coil. In some such implementations the personal medical device may have an active radio transmission capability, such as a Radio Access Technology, Device-to-Device, a proprietary radio, a beacon having a sleep mode, etc.

According to some implementations, a control system of the display device 40 may operate the induction coil 705 to provide metal detection functionality. For example, the control system may be capable of controlling the induction coil 705 to provide metal detection functionality according to pulse induction. A personal medical device, such as an IMD, will generally include at least some metal components (such as a battery), which may be detected according to such metal detection functionality.

Figure 8A:
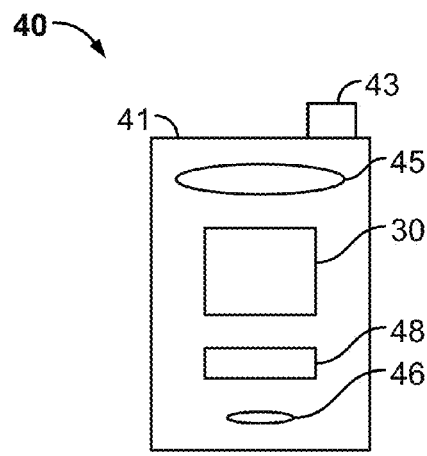
FIGS. 8A and 8B show examples of system block diagrams illustrating a display device that includes a sensor system and a control system as disclosed herein.
Figure 8B:
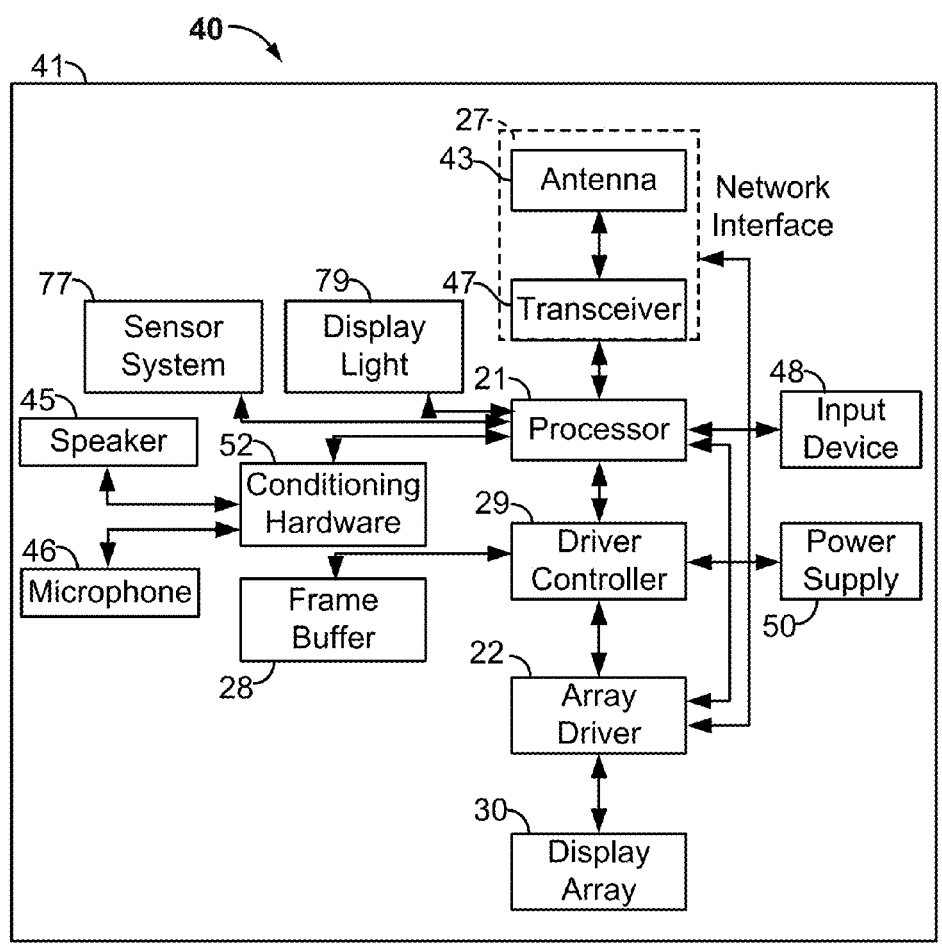

FIGS. 8A and 8B show examples of system block diagrams illustrating a display device that includes a sensor system and a control system as disclosed herein. The display device 40 can be, for example, a cellular or mobile telephone. However, the same components of the display device 40 or slight variations thereof are also illustrative of various types of display devices such as televisions, computers, tablets, e-readers, hand-held devices and portable media devices.

The display device 40 includes a housing 41, a display 30, an antenna 43, a speaker 45, an input device 48 and one or more microphones 46. The housing 41 can be formed from any of a variety of manufacturing processes, including injection molding and vacuum forming. In addition, the housing 41 may be made from any of a variety of materials, including, but not limited to: plastic, metal, glass, rubber and ceramic, or a combination thereof. The housing 41 can include removable portions (not shown) that may be interchanged with other removable portions of different color, or containing different logos, pictures, or symbols.

The display 30 may be any of a variety of displays, including a bi-stable or analog display, as described herein. The display 30 also can include a flat-panel display, such as plasma, EL, OLED, STN LCD, or TFT LCD, or a non-flat-panel display, such as a CRT or other tube device. In addition, the display 30 can include an interferometric modulator (IMOD) based display.

The components of the display device 40 are schematically illustrated in FIG. 8B. The display device 40 includes a housing 41 and can include additional components at least partially enclosed therein. For example, the display device 40 includes a network interface 27 that includes an antenna 43 which can be coupled to a transceiver 47. The network interface 27 may be a source for image data that could be displayed on the display device 40. Accordingly, the network interface 27 is one example of an image source module, but the processor 21 and the input device 48 also may serve as an image source module. The transceiver 47 is connected to a processor 21, which is connected to conditioning hardware 52. The conditioning hardware 52 may be capable of conditioning a signal (such as filter or otherwise manipulate a signal). The conditioning hardware 52 can be connected to a speaker 45 and a microphone 46. The processor 21 also can be connected to an input device 48 and a driver controller 29. The driver controller 29 can be coupled to a frame buffer 28, and to an array driver 22, which in turn can be coupled to a display array 30. One or more elements in the display device 40, including elements not specifically depicted in FIG. 8B, can be capable of functioning as a memory device and be capable of communicating with the processor 21. In some implementations, a power supply 50 can provide power to substantially all components in the particular display device 40 design.

In this example, the display device 40 includes a sensor system 77. According to some implementations, the sensor system 77 may include one or more cameras. In some examples, the sensor system 77 includes an ultrasonic sensor system. The ultrasonic sensor system may include one or more PMUT arrays. In some implementations, at least a portion of the ultrasonic sensor system may be disposed behind the display 30. In some such implementations, a ultrasonic sensor system may be disposed behind only part of the display 30, whereas in other implementations a ultrasonic sensor system may be disposed behind substantially all of the area of the display 30. In some implementations, at least a portion of ultrasonic sensor system may be included within one or more display pixels of display array 30. The processor 21 may be a portion of a control system that is capable of controlling the sensor system 77 (at least in part), as described herein. Accordingly, a control system 110 as described elsewhere herein may include the processor 21 and/or other elements of the display device 40, such as TFTs.

In some implementations, the processor 21 (and/or another element of the control system 110) may be capable of providing input for controlling the display device 40 according to one or more gestures detected when a PMUT array of the sensor system 77 is operating in a low-frequency mode. According to some implementations, the processor 21 (and/or another element of the control system 110) may be capable of controlling a PMUT array of the sensor system 77 to provide ultrasonic ranging functionality, e.g., when the PMUT array is operating in a low-frequency mode. In some implementations, the processor 21 (and/or another element of the control system 110) may be capable of providing input for controlling the display device 40 according to one or more touch locations and/or movements determined when a PMUT array of the sensor system 77 is operating in a medium-frequency mode. In some implementations, the processor 21 (and/or another element of the control system 110) may be capable of providing input for controlling the display device 40 according to fingerprint data or stylus input data determined when a PMUT array of the sensor system 77 is operating in a high-frequency mode. According to some implementations, the processor 21 (and/or another element of the control system 110) may be capable of controlling a PMUT array of the sensor system 77 to provide beam-steering functionality.

The network interface 27 includes the antenna 43 and the transceiver 47 so that the display device 40 can communicate with one or more devices over a network. The network interface 27 also may have some processing capabilities to relieve, for example, data processing requirements of the processor 21. The antenna 43 can transmit and receive signals. In some implementations, the antenna 43 transmits and receives RF signals according to the IEEE 16.11 standard, including IEEE 16.11(a), (b), or (g), or the IEEE 802.11 standard, including IEEE 802.11a, b, g, n, and further implementations thereof. In some other implementations, the antenna 43 transmits and receives RF signals according to the Bluetooth® standard. In the case of a cellular telephone, the antenna 43 can be designed to receive code division multiple access (CDMA), frequency division multiple access (FDMA), time division multiple access (TDMA), Global System for Mobile communications (GSM), GSM/General Packet Radio Service (GPRS), Enhanced Data GSM Environment (EDGE), Terrestrial Trunked Radio (TETRA), Wideband-CDMA (W-CDMA), Evolution Data Optimized (EV-DO), 1×EV-DO, EV-DO Rev A, EV-DO Rev B, High Speed Packet Access (HSPA), High Speed Downlink Packet Access (HSDPA), High Speed Uplink Packet Access (HSUPA), Evolved High Speed Packet Access (HSPA+), Long Term Evolution (LTE), AMPS, or other known signals that are used to communicate within a wireless network, such as a system utilizing 3G, 4G or 5G technology. The transceiver 47 can pre-process the signals received from the antenna 43 so that they may be received by and further manipulated by the processor 21.

The transceiver 47 also can process signals received from the processor 21 so that they may be transmitted from the display device 40 via the antenna 43.

In some implementations, the transceiver 47 can be replaced by a receiver. In addition, in some implementations, the network interface 27 can be replaced by an image source, which can store or generate image data to be sent to the processor 21. The processor 21 can control the overall operation of the display device 40. The processor 21 receives data, such as compressed image data from the network interface 27 or an image source, and processes the data into raw image data or into a format that can be readily processed into raw image data. The processor 21 can send the processed data to the driver controller 29 or to the frame buffer 28 for storage. Raw data typically refers to the information that identifies the image characteristics at each location within an image. For example, such image characteristics can include color, saturation and gray-scale level.

The processor 21 can include a microcontroller, CPU, or logic unit to control operation of the display device 40. The conditioning hardware 52 may include amplifiers and filters for transmitting signals to the speaker 45, and for receiving signals from the microphone 46. The conditioning hardware 52 may be discrete components within the display device 40, or may be incorporated within the processor 21 or other components.

The driver controller 29 can take the raw image data generated by the processor 21 either directly from the processor 21 or from the frame buffer 28 and can re-format the raw image data appropriately for high speed transmission to the array driver 22. In some implementations, the driver controller 29 can re-format the raw image data into a data flow having a raster-like format, such that it has a time order suitable for scanning across the display array 30. Then the driver controller 29 sends the formatted information to the array driver 22. Although a driver controller 29, such as an LCD controller, is often associated with the system processor 21 as a stand-alone Integrated Circuit (IC), such controllers may be implemented in many ways. For example, controllers may be embedded in the processor 21 as hardware, embedded in the processor 21 as software, or fully integrated in hardware with the array driver 22.

The array driver 22 can receive the formatted information from the driver controller 29 and can re-format the video data into a parallel set of waveforms that are applied many times per second to the hundreds, and sometimes thousands (or more), of leads coming from the display's x-y matrix of display elements.

In some implementations, the driver controller 29, the array driver 22, and the display 30 are appropriate for any of the types of displays described herein. For example, the driver controller 29 can be a conventional display controller or an IMOD display element controller, such as a multi-state IMOD (MS-IMOD) display element controller). Additionally, the array driver 22 can be a conventional driver or a bi-stable display driver (such as an MS-IMOD display element driver). Moreover, the display 30 can be a conventional display array or a bi-stable display array (such as a display including an array of IMOD display elements). In some implementations, the driver controller 29 can be integrated with the array driver 22. Such an implementation can be useful in highly integrated systems, for example, mobile phones, portable-electronic devices, watches or small-area displays.

In some implementations, the input device 48 can be capable of allowing, for example, a user to control the operation of the display device 40. The input device 48 can include a keypad, such as a QWERTY keyboard or a telephone keypad, a button, a switch, a rocker, a touch-sensitive screen, a touch-sensitive screen integrated with the display array 30, or a pressure- or heat-sensitive membrane. The microphone 46 can be capable of functioning as an input device for the display device 40. In some implementations, voice commands through the microphone 46 can be used for controlling operations of the display device 40.

The power supply 50 can include a variety of energy storage devices. For example, the power supply 50 can be a rechargeable battery, such as a nickel-cadmium battery or a lithium-ion battery. In implementations using a rechargeable battery, the rechargeable battery may be chargeable using power coming from, for example, a wall socket or a photovoltaic device or array. Alternatively, the rechargeable battery can be wirelessly chargeable. The power supply 50 also can be a renewable energy source, a capacitor, or a solar cell, including a plastic solar cell or solar-cell paint. The power supply 50 also can be capable of receiving power from a wall outlet.

In some implementations, control programmability resides in the driver controller 29 which can be located in several places in the electronic display system. In some other implementations, control programmability resides in the array driver 22. The above-described optimization may be implemented in any number of hardware and/or software components and in various configurations.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that can be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. Additionally, a person having ordinary skill in the art will readily appreciate, the terms "upper" and "lower", "over" and "under", and "overlying" and "underlying" are sometimes used for ease of describing the figures, and indicate relative positions corresponding to the orientation of the figure on a properly oriented page, and may not reflect the proper orientation of the device as implemented.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

The invention claimed is:

1. A mobile device, comprising:
    a sensor system that includes an ultrasonic sensor system; and
    a control system coupled to the sensor system, the control system being capable of:
        determining, based at least in part on signals from the ultrasonic sensor system, whether a personal medical device is within a predetermined distance from the mobile device; and
        adjusting one or more mobile device settings in response to a determination that the personal medical device is within the predetermined distance of the mobile device, and
    wherein the control system is further capable of:
        determining, based on signals received from the sensor system, a position of at least a portion of a person's body;
        controlling the ultrasonic sensor system to obtain ultrasonic image data from the portion of the person's body; and
        determining, based at least in part on the ultrasonic image data, whether the personal medical device is an implantable medical device that is within the portion of the person's body.

2. The mobile device of claim 1, wherein the sensor system includes at least one camera and wherein the control system is capable of determining that the personal medical device is within the predetermined distance based, at least in part, on data received from the at least one camera.

3. The mobile device of claim 1, wherein the sensor system includes at least one camera and wherein the control system is capable of:
    receiving data from the at least one camera; and
    determining the position of at least the portion of the person's body based, at least in part, on the data received from the at least one camera.

4. The mobile device of claim 1, wherein the control system is capable of controlling the ultrasonic sensor system to cause transmitted ultrasonic waves to be transmitted in one or more selected directions.

5. The mobile device of claim 4, wherein the ultrasonic sensor system includes an array of individually controllable piezoelectric micromachined ultrasonic transducers (PMUTs) and wherein the control system is capable of controlling the array of PMUTs to cause constructive interference in the one or more selected directions.

6. The mobile device of claim 1, wherein the sensor system includes apparatus for receiving radio frequency (RF) signals emitted by the personal medical device.

7. The mobile device of claim 6, wherein the mobile device includes an RF transmitter capable of transmitting an RF signal for causing a responsive RF signal from a passive radio frequency identification (RFID) tag or a near-field communication tag on the personal medical device.

8. The mobile device of claim 1, wherein the ultrasonic sensor system is capable of receiving ultrasonic signals that are emitted from an active ultrasonic transmitter on the personal medical device and wherein the control system is capable of determining, based at least in part on the ultrasonic signals, whether the personal medical device is within the predetermined distance.

9. The mobile device of claim 1, wherein the control system is capable of determining the predetermined distance based, at least in part, on one or more contextual indications.

10. The mobile device of claim 1, further comprising at least one induction coil, wherein the control system is capable of determining the predetermined distance based, at least in part, on input from the at least one induction coil.

11. The mobile device of claim 10, wherein the control system is capable of controlling the at least one induction coil to provide metal detection functionality.

12. The mobile device of claim 10, wherein the control system is capable of controlling the at least one induction coil to provide passive or active near-field communications (NFC) functionality.

13. The mobile device of claim 1, wherein the predetermined distance corresponds with an interference range within which electromagnetic interference from the mobile device can cause interference with operation of the personal medical device.

14. The mobile device of claim 1, further comprising a user interface, wherein the control system is capable of varying the predetermined distance according to one or more factors selected from a list of factors consisting of input received via the user interface, information regarding a device type of the personal medical device and signals from the ultrasonic sensor system.

15. The mobile device of claim 1, further comprising one or more microphones, wherein the control system is capable of determining whether the personal medical device is within the predetermined distance based, at least in part, on microphone data received from the one or more microphones.

16. A system, comprising:
  a sensor system that includes an ultrasonic sensor system; and
  control means configured for communication with the sensor system, the control means including means for:
    determining, based at least in part on signals from the ultrasonic sensor system, whether a personal medical device is within a predetermined distance from a mobile device; and
    adjusting one or more mobile device settings in response to a determination that the personal medical device is within the predetermined distance of the mobile device, and
  wherein the control means further comprises means for:
    determining, based on signals received from the sensor system, a position of at least a portion of a person's body;
    controlling the ultrasonic sensor system to obtain ultrasonic image data from the portion of the person's body; and
    determining, based at least in part on the ultrasonic image data, whether the personal medical device is an implantable medical device that is within the portion of the person's body.

17. The mobile device of claim 16, wherein the sensor system includes a camera and wherein the control means includes means for determining that the personal medical device is within the predetermined distance based, at least in part, on data received from the camera.

18. A method of controlling a mobile device, comprising:
  determining, based at least in part on signals from a sensor system that includes an ultrasonic sensor system, whether a personal medical device is within a predetermined distance from the mobile device; and
  adjusting one or more mobile device settings in response to a determination that the personal medical device is within the predetermined distance of the mobile device, and wherein the method further comprises:
    determining, based on signals received from the sensor system, a position of at least a portion of a person's body;
    controlling the ultrasonic sensor system to obtain ultrasonic image data from the portion of the person's body; and
    determining, based at least in part on the ultrasonic image data, whether the personal medical device is an implantable medical device that is within the portion of the person's body.

19. The method of claim 18, wherein the sensor system includes at least one camera, further comprising determining that the personal medical device is within the predetermined distance based, at least in part, on data received from the at least one camera.

20. A non-transitory medium having software stored thereon, the software including instructions for controlling a mobile device for:
  determining, based at least in part on signals from a sensor system that includes an ultrasonic sensor system, whether a personal medical device is within a predetermined distance from the mobile device; and
  adjusting one or more mobile device settings in response to a determination that the personal medical device is within the predetermined distance of the mobile device, and wherein the software further includes instructions for controlling the mobile device for:
    determining, based on signals received from the sensor system, a position of at least a portion of a person's body;
    controlling the ultrasonic sensor system to obtain ultrasonic image data from the portion of the person's body; and
    determining, based at least in part on the ultrasonic image data, whether the personal medical device is an implantable medical device that is within the portion of the person's body.

21. The non-transitory medium of claim 20, wherein the sensor system includes at least one camera and wherein the software includes instructions for determining that the personal medical device is within the predetermined distance based, at least in part, on data received from the at least one camera.

* * * * *